United States Patent
Prince

(10) Patent No.: US 7,458,318 B2
(45) Date of Patent: Dec. 2, 2008

(54) OFF-AXIS ILLUMINATION ASSEMBLY AND METHOD

(75) Inventor: David P. Prince, Wakefield, RI (US)

(73) Assignee: Speedline Technologies, Inc., Franklin, MA (US)

( * ) Notice: Subject to any disclaimer, the term of this patent is extended or adjusted under 35 U.S.C. 154(b) by 360 days.

(21) Appl. No.: 11/345,432

(22) Filed: Feb. 1, 2006

(65) Prior Publication Data

US 2007/0175343 A1    Aug. 2, 2007

(51) Int. Cl.
    B05C 17/04 (2006.01)

(52) U.S. Cl. ............... 101/123; 101/126; 101/129; 382/108; 356/237.1; 356/615

(58) Field of Classification Search ............ 101/114, 101/123, 124, 126, 129; 382/108; 358/1.18; 356/237.1, 239.7, 614, 615
See application file for complete search history.

(56) References Cited

U.S. PATENT DOCUMENTS

| | | |
|---|---|---|
| 5,058,178 A | 10/1991 | Ray |
| 5,060,063 A | 10/1991 | Freeman |
| 5,157,438 A | 10/1992 | Beale |
| 5,278,012 A | 1/1994 | Yamanaka et al. |
| RE34,615 E | 5/1994 | Freeman |
| 5,455,870 A | 10/1995 | Sepai et al. |
| 5,752,446 A | 5/1998 | Squibb |
| 5,943,089 A | 8/1999 | Douglas |
| 6,198,529 B1 | 3/2001 | Clark, Jr. et al. |
| 6,621,517 B1 | 9/2003 | Squibb |
| 6,738,505 B1 | 5/2004 | Prince |
| 6,810,138 B1 | 10/2004 | Schanz |
| 6,891,967 B2 | 5/2005 | Prince |
| 7,028,391 B2 | 4/2006 | Pham-Van-Diep et al. |
| 7,239,399 B2 * | 7/2007 | Duquette et al. ............ 356/614 |
| 2007/0102477 A1 | 5/2007 | Prince |

FOREIGN PATENT DOCUMENTS

| | | |
|---|---|---|
| GB | 2 403 003 A | 12/2004 |
| WO | 02/097534 A2 | 12/2002 |

OTHER PUBLICATIONS

Patent Abstracts of Japan; JP 2002234131 A (Sony Corp.); Aug. 20, 2002; 1 pg.

(Continued)

*Primary Examiner*—Ren Yan
(74) *Attorney, Agent, or Firm*—Lowrie, Lando & Anastasi, LLP

(57) ABSTRACT

A stencil printer is provided for depositing solder paste onto a surface of an electronic substrate. The stencil printer includes a frame and a stencil coupled to the frame. The stencil has a plurality of apertures formed therein. The stencil printer further includes a dispenser coupled to the frame. The stencil and the dispenser are adapted to deposit solder paste onto the electronic substrate. The stencil printer further includes an imaging system constructed and arranged to capture an image of the electronic substrate. The imaging system includes a camera assembly, an on-axis illumination assembly adapted to generate light substantially along a first axis generally perpendicular to the surface of the electronic substrate, and an off-axis illumination assembly adapted to generate rays of light substantially along a second axis extending at an angle with respect to the first axis. A controller is coupled to the imaging system to control movement of the imaging system to capture an image.

27 Claims, 12 Drawing Sheets

OTHER PUBLICATIONS

International Search Report for PCT/US2006/043166 mailed Feb. 2, 2007.

Ekra-Eva™ Vision-System; http://www.ekra.com/pages/eva.html; 1 page.

International Search Report for PCT/US2007/002925 mailed Jan. 16, 2008.

* cited by examiner

OFF-AXIS ILLUMINATION ASSEMBLY AND METHOD

FIELD OF THE INVENTION

The present invention relates to apparatuses and processes for dispensing material, and more particularly to an apparatus and process for printing solder paste through a screen or stencil printer onto an electronic substrate, such as a printed circuit board.

BACKGROUND OF THE INVENTION

In typical surface-mount circuit board manufacturing operations, a stencil printer is used to print solder paste onto a circuit board. Typically, a circuit board having a pattern of pads or other conductive surfaces onto which solder paste will be deposited is automatically fed into the stencil printer and one or more small holes or marks on the circuit board, called fiducials, is used to align the circuit board with a stencil or screen of the printer prior to the printing of solder paste onto the circuit board. After the circuit board is aligned, the board is raised to the stencil (or in some configurations, the stencil is lowered to the circuit board), solder paste is dispensed onto the stencil, and a wiper blade (or squeegee) traverses the stencil to force the solder paste through apertures formed in the stencil and onto the board.

In some prior art stencil printers, a dispensing head delivers solder paste between first and second wiper blades, wherein during a print stroke one of the wiper blades is used to move or roll solder paste across the stencil. The first and second wiper blades are used on alternating boards to continually pass the roll of solder paste over the apertures of a stencil to print each successive circuit board. The wiper blades are typically at an angle with respect to the stencil to apply downward pressure on the solder paste to force the solder paste through the apertures of the stencil. In other prior art stencil printers, the dispensing head is pressurized to force solder paste through the apertures, and the wiper blades are employed to scrape excess solder paste from the stencil during a print stroke.

After solder paste is deposited onto the circuit board, an imaging system is employed to take images of areas of the circuit board and/or the stencil for, in certain instances, the purpose of inspecting the accuracy of the deposit of solder paste on the pads of the circuit board. Another application of the imaging system involves the aforementioned aligning of the stencil and the circuit board prior to printing in order to register the openings of the stencil with the electronic pads of the circuit board. Such imaging systems are disclosed in U.S. Pat. Nos. RE34,615 and 5,060,063, both to Freeman, which are owned by the assignee of the present invention and incorporated herein by reference. An improved imaging system is disclosed in pending application Ser. No. 11/272,192, entitled IMAGING SYSTEM AND METHOD FOR A STENCIL PRINTER, filed on Nov. 10, 2005, to Prince, which is owned by the assignee of the present invention and incorporated herein by reference.

Consistent modeling of solder paste on a substrate, e.g., the circuit board, is required to facilitate the optimum two-dimensional imaging performance of the vision system, as well as subsequent inspections based on these images, irrespective of variations in geometry, definition, or general qualities of the deposit being imaged. Well-defined solder paste deposits have nearly vertical sides and relatively flat top surfaces that are perpendicular to the optical viewing axis (i.e., an axis generally perpendicular to a plane of the circuit board). Finely textured paste surfaces having this generally perpendicular orientation may be imaged with relative consistency using on-axis illumination alone. With on-axis illumination, the strongest components of scattered light from the top surface of the solder paste deposit are directed back along the optical viewing path and are collected by the imaging system.

In contrast, when on-axis illumination strikes a surface that is not generally perpendicular to the angle of incidence, the strongest components of scattered light from the surface are directed away, or off-axis, from the optical or on-axis viewing path and are not collected by the imaging system. Specifically, it is shown that the sloped sides and irregular top surfaces of poorly shaped solder paste deposits are less efficiently illuminated and therefore more difficult to view using only on-axis illumination only.

SUMMARY OF THE INVENTION

The invention will be more fully understood after a review of the following figures, detailed description and claims.

One aspect of the invention is directed to a stencil printer for depositing solder paste onto a surface of an electronic substrate. The stencil printer comprises a frame and a stencil coupled to the frame. The stencil has a plurality of apertures formed therein. The stencil printer further comprises a dispenser coupled to the frame. The stencil and the dispenser are constructed and arranged to deposit solder paste onto the electronic substrate. The stencil printer further comprises an imaging system constructed and arranged to capture an image of the electronic substrate. The imaging system includes a camera assembly, an on-axis illumination assembly adapted to generate light substantially along a first axis generally perpendicular to the surface of the electronic substrate, and an off-axis illumination assembly adapted to generate rays of light substantially along a second axis extending at an angle with respect to the first axis. A controller is coupled to the imaging system to control movement of the imaging system to capture an image.

Embodiments of the stencil printer may include the provision of the on-axis illumination assembly of the imaging system having an optical path adapted to direct light between the on-axis illumination assembly, the electronic substrate, and the camera assembly. The imaging system comprises a mounting bracket adapted to support the off-axis illumination assembly. The off-axis illumination assembly comprises a light generating module supported by the mounting bracket, which, in certain embodiments, may comprise at least one light emitting diode. The off-axis illumination assembly further comprises a lens configured to direct the rays of light, the lens being secured to the mounting bracket. The lens comprises one or more refractive surfaces adapted to direct light from the light generating module along a prescribed path. The camera assembly comprises a camera and a lens assembly adapted to direct an image to the camera. The optical path comprises a beam splitter and a mirror. The on-axis illumination assembly comprises at least one light emitting diode. In certain embodiments, the imaging system is constructed and arranged to capture an image of solder paste on a pad of the electronic substrate within the area. The controller comprises a processor programmed to perform texture recognition of the electronic substrate to determine the accuracy of the solder paste deposits on the pads of the electronic substrate.

Another aspect of the invention is directed to an imaging system for capturing an image of a surface of an electronic substrate. The imaging system comprises a housing and a camera assembly coupled to the housing. The camera assembly is adapted to capture an image of the electronic substrate.

An on-axis illumination assembly is coupled to the housing, with the on-axis illumination assembly being adapted to generate light substantially along a first axis generally perpendicular to the surface of the electronic substrate. An off-axis illumination assembly is coupled to the housing, with the off-axis illumination assembly being adapted to generate rays of light substantially along a second axis extending at an angle with respect to the first axis.

Embodiments of the imaging system may include an optical path adapted to direct light between the on-axis illumination assembly, the electronic substrate, and the camera assembly. The housing of the imaging system comprises a mounting bracket adapted to support the off-axis illumination assembly. The off-axis illumination assembly comprises a light generating module supported by the mounting bracket, which, in certain embodiments, comprises at least one light emitting diode. The off-axis illumination assembly further comprises a lens configured to direct the rays of light, the lens being secured by the mounting bracket. The lens comprises a refractive surface adapted to direct light from the light generating module to create the rays of light. The optical path may include at least one beam splitter and a mirror. The camera assembly may include a camera and a lens assembly adapted to direct an image to the camera. The on-axis illumination assembly comprises at least one light emitting diode. The imaging system is constructed and arranged to capture an image of solder paste on a pad of an electronic substrate.

Yet another aspect of the invention is directed to a method for dispensing solder paste onto a surface of an electronic substrate. The method comprises: delivering an electronic substrate to a stencil printer; performing a print operation to print solder paste onto the surface of the electronic substrate; illuminating at least one area of the electronic substrate with on-axis light that extends substantially along a first axis generally perpendicular to the surface of the electronic substrate; illuminating the at least one area of the electronic substrate with off-axis light that extends substantially along a second axis extending at an angle with respect to the first axis; and capturing an image of the at least one area of the electronic substrate.

Embodiments of the method may further comprise positioning the electronic substrate in a print position, and positioning a stencil onto the electronic substrate. The capturing an image of at least one area of the electronic substrate may employ an imaging system. The method may further comprise moving the imaging system from a first position that captures an image of a first area to a second position that captures an image of a second area. In addition, the method may further comprise performing a texture recognition sequence of the at least one area of the electronic substrate to determine the accuracy of the solder paste deposits on the pads of the electronic substrate. In some embodiments, the method further comprises illuminating the at least one area of the electronic substrate with off-axis light that extends substantially along a third axis extending at an angle with respect to the first axis.

Another aspect of the invention is directed to a stencil printer for depositing solder paste onto a surface of an electronic substrate. The stencil printer comprises a frame and a stencil coupled to the frame. In one embodiment, the stencil has a plurality of apertures formed therein. A dispenser is coupled to the frame, with the stencil and the dispenser being constructed and arranged to deposit solder paste onto the electronic substrate. An imaging system is constructed and arranged to capture an image of the electronic substrate. The imaging system comprises a camera assembly and an on-axis illumination assembly adapted to generate light substantially along a first axis generally perpendicular to the surface of the electronic substrate. The on-axis illumination assembly includes an optical path adapted to reflect light between the on-axis illumination assembly, the electronic substrate, and the camera assembly. The imaging system further comprises means for generating rays of light along a second axis extending substantially at an angle with respect to the first axis. A controller is coupled to the imaging system to control movement of the imaging system to capture an image.

Embodiments of the stencil printer may further include the means for generating rays of light comprising an off-axis illumination assembly. The imaging system further comprises a mounting bracket adapted to support the off-axis illumination assembly. The off-axis illumination assembly comprises a light generating module supported by the mounting bracket, and, in certain embodiments, the light generating module comprises a light emitting diode. The off-axis illumination assembly comprises a lens configured to direct the rays of light, the lens being secured to the mounting bracket and having at least one surface adapted to direct light from the light generating module to create the rays of light. In other embodiments, the camera assembly comprises a camera and a lens assembly adapted to direct an image to the camera.

BRIEF DESCRIPTION OF THE DRAWINGS

In the drawings, like reference characters refer to the same or similar parts throughout the different views. The drawings are not necessarily to scale, emphasis instead being placed upon illustrating particular principles, discussed below.

DETAILED DESCRIPTION OF THE INVENTION

For purposes of illustration, embodiments of the present invention will now be described with reference to a stencil printer used to print solder paste onto a circuit board. One skilled in the art will appreciate that embodiments of the present invention are not limited to stencil printers that print solder paste onto circuit boards, but rather, may be used in other applications requiring dispensing of other viscous materials, such as glues, encapsulents, underfills, and other assembly materials suitable for attaching electronic components onto a circuit board. Thus, any reference to solder paste herein contemplates use of such other materials. Also, the terms "screen" and "stencil" may be used interchangeably herein to describe a device in a printer that defines a pattern to be printed onto a substrate.

Figure 1:
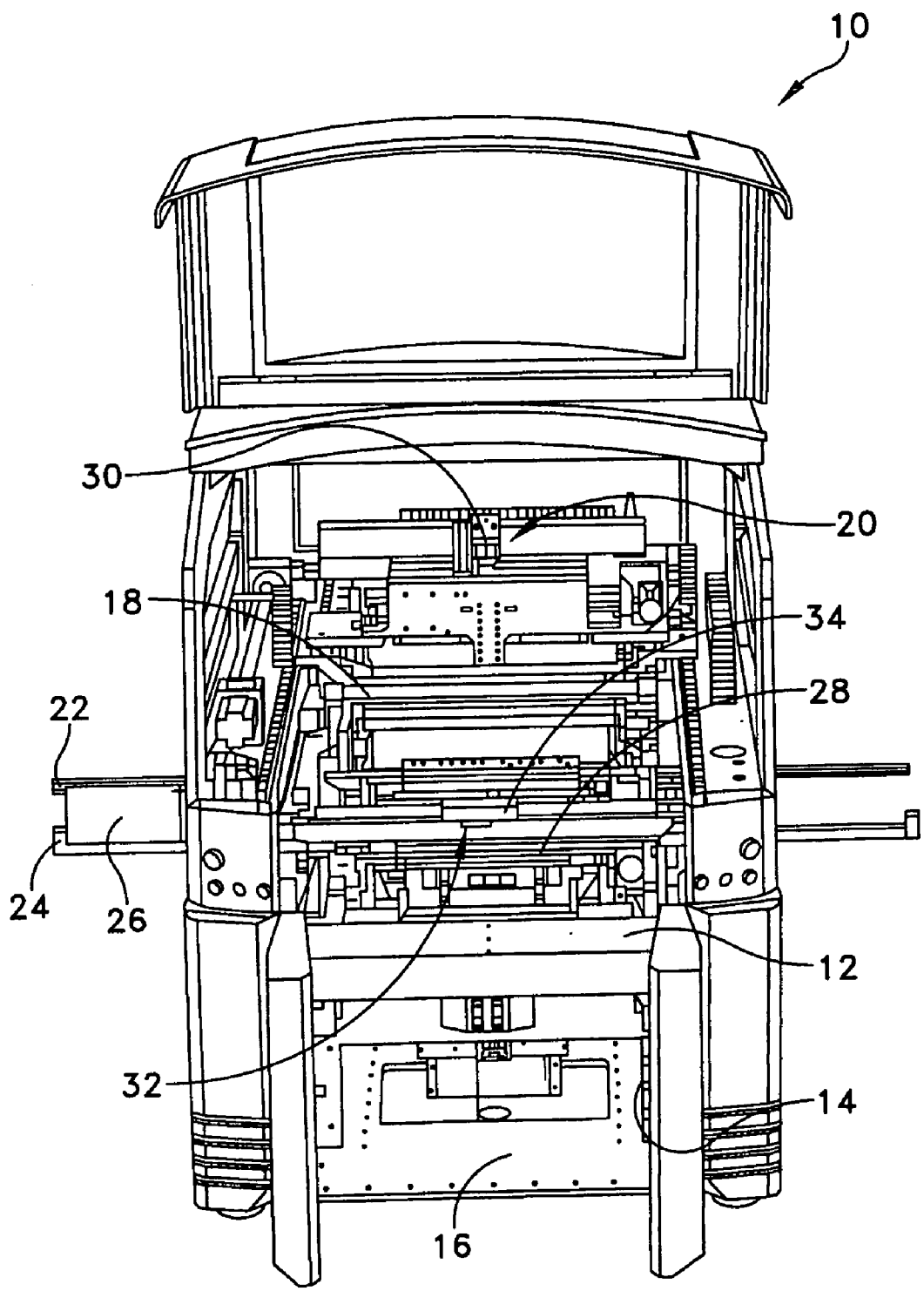
FIG. 1 is a front perspective view of a stencil printer of an embodiment of the present invention.

FIG. 1 shows a front perspective view of a stencil printer, generally indicated at 10, in accordance with one embodiment of the present invention. The stencil printer 10 includes a frame 12 that supports components of the stencil printer including a controller 14 located in a cabinet 16 of the stencil printer, a stencil 18, and a dispensing head, generally indicated at 20, for dispensing solder paste. The dispensing head 20 is movable along orthogonal axes by a gantry system (not designated) under the control of the controller 14 to allow printing of solder paste on a circuit board.

Stencil printer 10 also includes a conveyor system having rails 22, 24 for transporting a circuit board 26 to a printing position in the stencil printer 10. The stencil printer 10 has a support assembly 28 (e.g., pins, gel membranes, etc.) positioned beneath the circuit board 26 when the circuit board is in the dispensing position. The support assembly 28 is used to raise the circuit board 26 off of the rails 22, 24 to place the circuit board in contact with, or in close proximity to, the stencil 18 when printing is to occur.

In one embodiment, the dispensing head 20 is configured to receive at least one solder paste cartridge 30 that provides solder paste to the dispensing head during a printing operation. In one embodiment, the solder paste cartridge 30 is coupled to one end of a pneumatic air hose in the well known manner. The other end of the pneumatic air hose is attached to a compressor contained within the frame 12 of the stencil printer 10 that under the control of the controller 14 provides pressurized air to the cartridge 30 to force solder paste into the dispensing head 20 and onto the stencil 18. Other configurations for dispensing solder paste onto the stencil 18 may also be employed. For example, in another embodiment, mechanical devices, such as a piston, may be used in addition to, or in place of, air pressure to force the solder paste from the cartridge 30 into the dispensing head 20. In yet another embodiment, the controller 14 is implemented using a personal computer having a suitable operating system (e.g., Microsoft® DOS or Windows® NT) with application specific software to control the operation of the stencil printer 10 as described herein.

The stencil printer 10 operates as follows. A circuit board 26 is loaded into the stencil printer in a print position using the conveyor rails 22, 24. The dispensing head 20 is then lowered in the Z-direction until it is in contact with the stencil 18. The dispensing head fully traverses the stencil 18 in a first print stroke to force solder paste through apertures of the stencil and onto the circuit board 26. Once the dispensing head 20 has fully traversed the stencil 18, the circuit board 26 is transported by the conveyor rails 22, 24 from the stencil printer 10 so that a second, subsequent circuit board may be loaded into the stencil printer. To print on the second circuit board, the dispensing head 20 may be moved in a second print stroke across the stencil 18 in an opposite direction to that used for the first circuit board.

Figure 2:
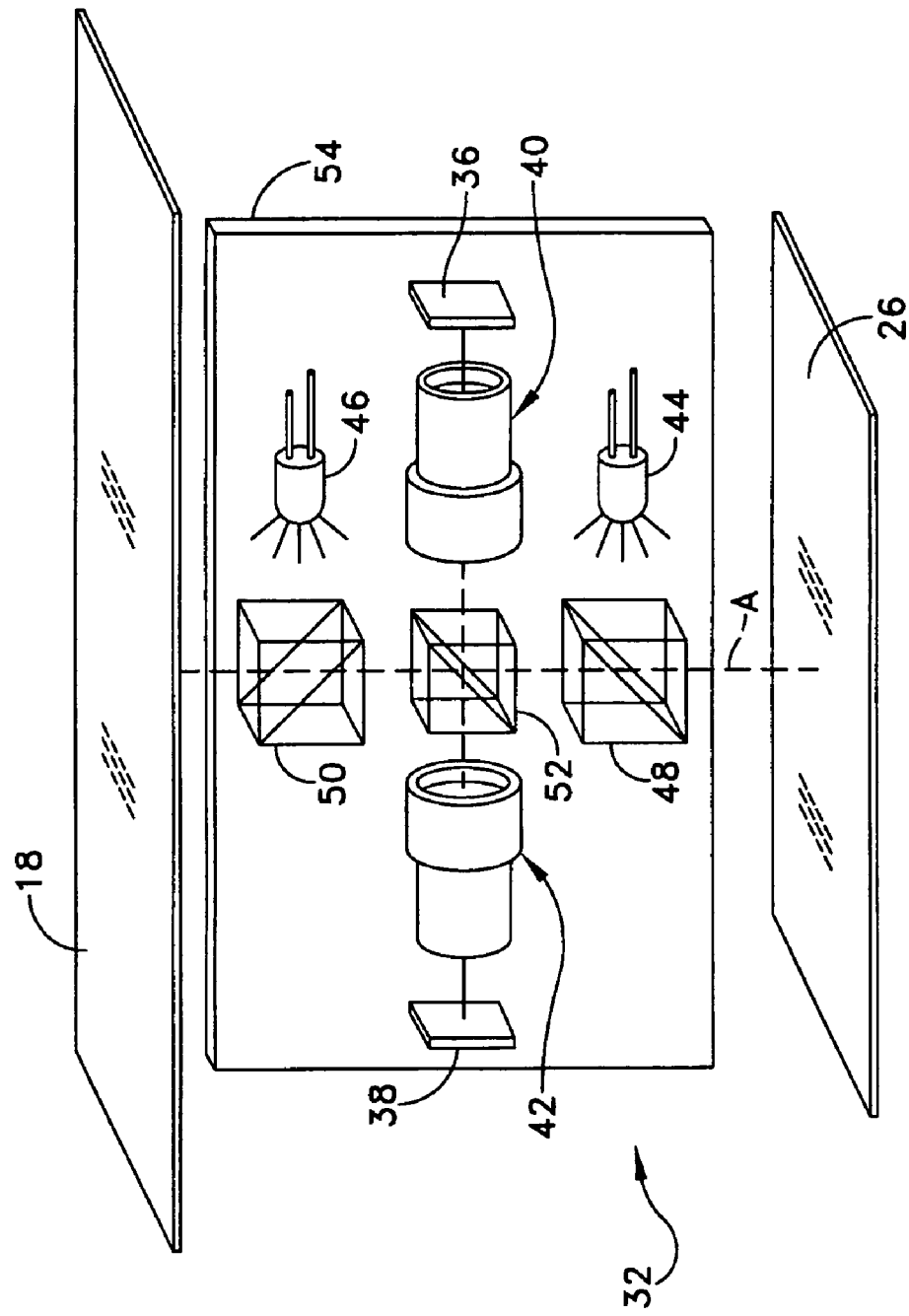
FIG. 2 is a schematic view of an imaging system of an embodiment of the present invention.

Referring to FIG. 2 in addition to FIG. 1, an imaging system of an embodiment of the present invention is generally designated at 32. As shown, the imaging system 32 is disposed between the stencil 18 and the circuit board 26, which in turn is supported by the support assembly 28 (FIG. 1). The imaging system 32 is coupled to a gantry system 34 (FIG. 1), which may be part of the gantry used to move the dispensing head 20 or provided separately within the stencil printer 10. The construction of the gantry system 34 used to move the imaging system 32 is well known in the art of inspection within a solder paste printer. The arrangement is such that the imaging system 32 may be located at any position below the stencil 18 and above the circuit board 26 to capture an image of predefined areas of the circuit board or the stencil, respectively. In other embodiments, when positioning the imaging system 32 outside the printing nest, the imaging system 32 may be located above or below the stencil 18 and the circuit board 26.

As shown in FIG. 2, in one embodiment, the imaging system comprises an optical assembly having two cameras 36, 38, two lens assemblies generally indicated at 40, 42, two illumination devices 44, 46, two beam splitters 48, 50, and a mirror assembly 52. In certain embodiments, the camera and a lens assembly may be configured together as a camera assembly. Such an assembly as well as the imaging system may also be referred to a video probe. A frame 54 supports the components of the imaging system 32. The cameras 36, 38 may be identical in construction with respect to one another, and, in one embodiment, each camera may be a digital CCD camera of the type that may be purchased from Opteon Corporation of Cambridge, Mass. under Model No. CHEAMD-PCACELA010100. Further description of the cameras 36, 38 will be provided below with reference to FIG. 3.

In one embodiment, the illumination devices 44, 46 may be one or more light emitting diodes (white light diodes) that are capable of generating an intense amount of light at their respective beam splitter 48 or 50. The illumination devices 44, 46 may be of the type sold by Nichia Corporation of Detroit, Mich. under Model No. NSPW310BSB1B2/ST. The beam splitters 48, 50 and the mirror assembly 52, which is a dual mirror with zero beam split, are well known in the art. In other embodiments, xenon and halogen lamps may be used to generate the light required. Fiber optics can also be used to convey light from the remote source to the point of use.

The beam splitters 48, 50 are designed to reflect a portion of the light generated by their respective illumination devices 44, 46 along a generally vertical axis A toward the circuit board 26 and the stencil 18, respectively, while further allowing a portion of the light reflected by the circuit board and the stencil pass through to the mirror assembly 52. As used herein, the illumination device 44, and the beam splitter 48 may be referred to as an on-axis illumination assembly, which is configured to direct light substantially along or parallel to the axis A, which is generally perpendicular to a plane of the circuit board 26. Reflected light from the circuit board 26 travels back through the beam splitter 48 and on to the mirror assembly 52 where it is redirected toward lens assembly 40 in order to capture an image of a predefined area of the circuit board.

The optical paths defined between the illumination devices 44, 46 and their respective cameras 36, 38 by means of beam splitters 48, 50 and mirror assembly 52 are well known to a person skilled in the art. As shown, the light reflected by the beam splitters 48, 50 toward their respective objects (i.e., the circuit board 26 and the stencil 18, respectively) extends substantially along or parallel to the axis A that is generally normal to the plane of the object. In one embodiment, the construction of the optical paths created by the beam splitters 48, 50 and the mirror assembly 52 is substantially similar to the paths disclosed in U.S. Pat. No. 5,060,063, except that mirror is a full mirror (due to the provision of the two cameras 36, 38) and does not allow part of the light to pass therethrough.

Figure 3:
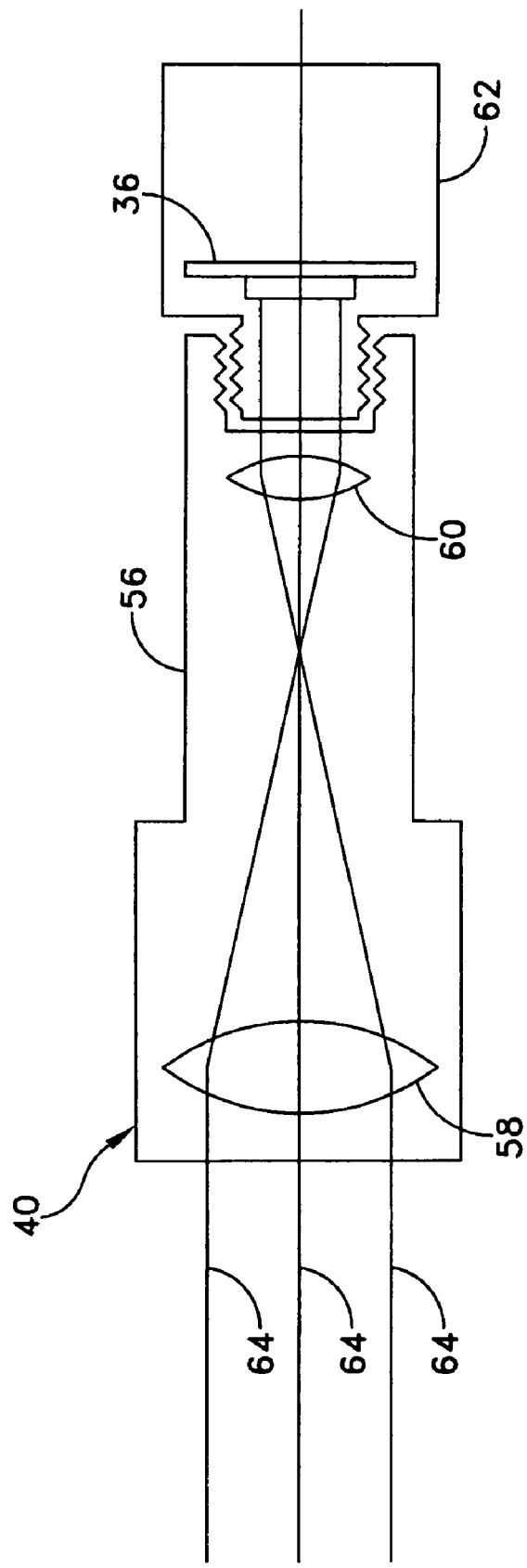
FIG. 3 is an enlarged schematic view of a camera and lens assembly of the imaging system illustrated in FIG. 2.

Referring to FIG. 3, camera 36 and lens assembly 40 are illustrated. As discussed above, camera 38 may be identical in construction to camera 36. In addition, the construction of lens assembly 42 may be identical in construction to lens assembly 40. Accordingly, the following discussion of camera 36 and lens assembly 40 generally applies for camera 38 and lens assembly 42, respectively, and, as discussed above, such an assembly may be referred to as a camera assembly or video probe. As shown schematically, the lens assembly 40 includes a housing 56, a pair of lenses 58, 60 disposed within the housing and an aperture (not shown) disposed between the lenses. The lenses 58, 60 together provide the telecentric capability of the lens assembly 40. The collective lens assembly 40 may also be referred to as a "lens," which is specifically referred to herein as the telecentric lens assembly.

The arrangement is such that light reflected from the mirror assembly 52 is directed to the lens assembly 40. Once in the lens assembly 40, the light passes through lens 58, through the aperture (not shown), through the second lens 60, and on to the light-sensitive region of the camera 36, where the image is formed. In one embodiment the CCD reader of the camera may include an electronic shutter. The camera 36, in part due to the telecentric lens assembly, is designed to view an entire predefined area without exhibiting significant distortion in any part of the image.

As shown in FIG. 3, the camera 36 is supported by a housing 62, which may be threadably attached to the housing 56 of the lens assembly 40. The housing 56 of the lens assembly 40 and the housing 62 of the camera 36 are in axial alignment with on another so that the image, which is represented in ray-form by lines 64, is accurately directed toward the camera. The housing 56 of the lens assembly 40 is suitably secured to the frame 54 of the imaging system.

The arrangement is such that when taking an image of the circuit board 26, the illumination device 44 generates an intense amount of light toward its respective beam splitter 48. This light is reflected by the beam splitter 48 toward the circuit board 26, and is then reflected back toward the mirror assembly 52. The mirror assembly 52 directs the light through the lens assembly 40 and to the camera 36, which captures the image of the predefined area of the circuit board 26. The image may be electronically stored or used in real-time so that the image may be manipulated and analyzed by the controller 14 to either detect a defective solder deposit or align the circuit board 26 with the stencil 18, for example.

Similarly, when taking an image of the stencil 18, the illumination device 46 generates a beam of light that is directed toward its respective beam splitter 50. The light is then directed toward the stencil 18 and reflects back through the beam splitter 50 to the mirror assembly 52. The light is then directed toward the telecentric lens assembly 42 and on to the camera 38 to capture the image of the predefined area of the stencil 18. Once captured, the area of the stencil 18 may be analyzed by the controller 14 for inspection purposes (e.g., detecting clogged apertures in the stencil, for example), or compared to an area of the circuit board 26 for alignment purposes. The inspection capability of the imaging system 32 will be described in greater detail below with reference to the description of a texture recognition program.

As discussed above, with respect to capturing an image of an area of the circuit board, the illumination device 44 is configured to direct light along or parallel to the axis A normal to the plane of the circuit board. Thus, the camera 38 is adapted to only capture images of light reflected from surfaces on the circuit board 26 that are normal to the direction of the light emitted onto the circuit board. Irregular, rounded or faceted surfaces, i.e., surfaces of solder paste deposits that are at an angle with respect to the plane of the circuit board, have a tendency to become less prominent as light is reflected away from the optical path.

Figure 4:
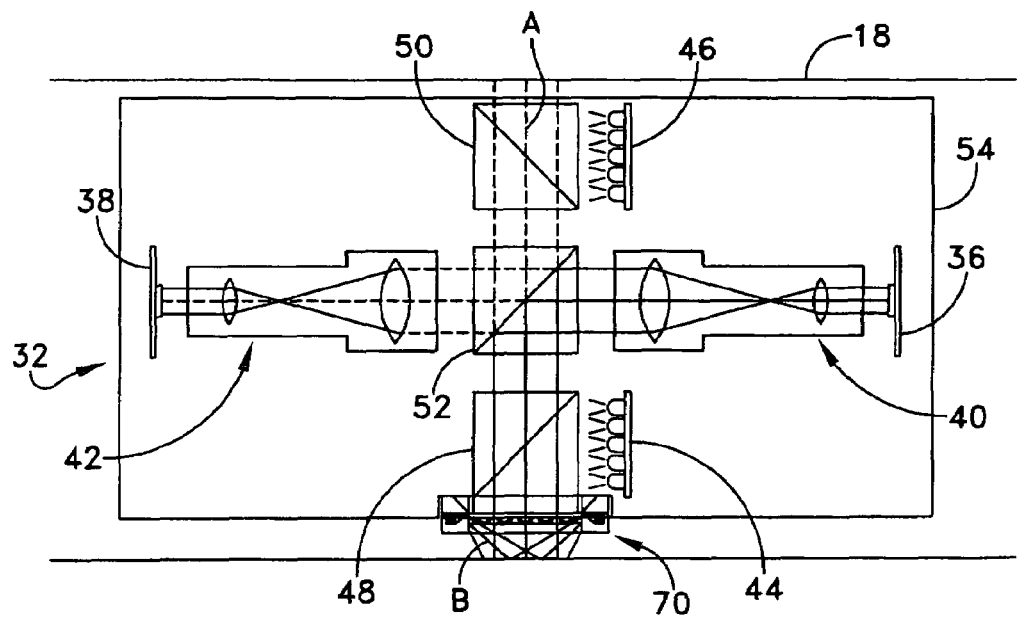
FIG. 4 is a schematic view of an imaging system of an embodiment of the invention incorporating an off-axis illumination assembly of an embodiment of the present invention.
Figure 5:
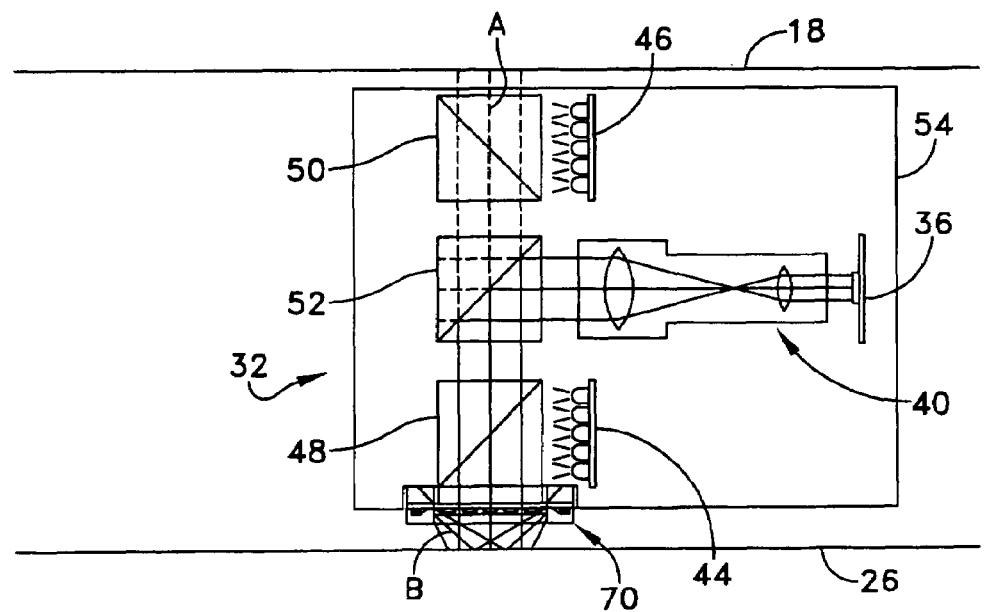
FIG. 5 is a schematic view of an imaging system of another embodiment of the invention incorporating an off-axis illumination assembly identical to the off-axis illumination assembly shown in FIG. 4.

Turning now to FIG. 4, there is generally indicated at 70 an off-axis illumination assembly of an embodiment of the present invention, which is mounted on or adjacent to the lowermost beam splitter 48. As will be discussed in greater detail below, the off-axis illumination assembly 70 is configured to direct rays of light generally along or parallel to an axis B extending at an angle (e.g., between 30 and 60 degrees) with respect to the axis A of light generated by the on-axis illumination assembly. The off-axis-illumination assembly 70 is designed to complement the direct illumination provided by the on-axis illumination assembly, thereby providing indirect light to more clearly see the rounded and faceted or otherwise irregular surfaces on the circuit board. As shown, the off-axis illumination assembly 70 is provided on the imaging system 32 employing two cameras 36, 38. However, as illustrated in FIG. 5, the off-axis illumination assembly 70 may be provided on an imaging system 34 employing only one camera 36 and still fall within the scope of the instant invention. Whether employing a single or dual camera arrangement, the controller 14 is adapted to control the movement of the imaging system 34 to capture an image of the circuit board 26.

One aspect of the off-axis illumination assembly 70 is that the assembly, in certain embodiments, may be configured to have an extremely low or narrow profile to fit within the space between the beam splitter 48 and the substrate, e.g., the circuit board 26. The off-axis illumination assembly 70 is designed to direct light onto the circuit board 26 at an extremely close working distance while maintaining considerable control of local angles of incidence and the distribution and balance of light across the target area. The off-axis illumination assembly 70 is further designed to direct light primarily by diffraction.

Figure 6:
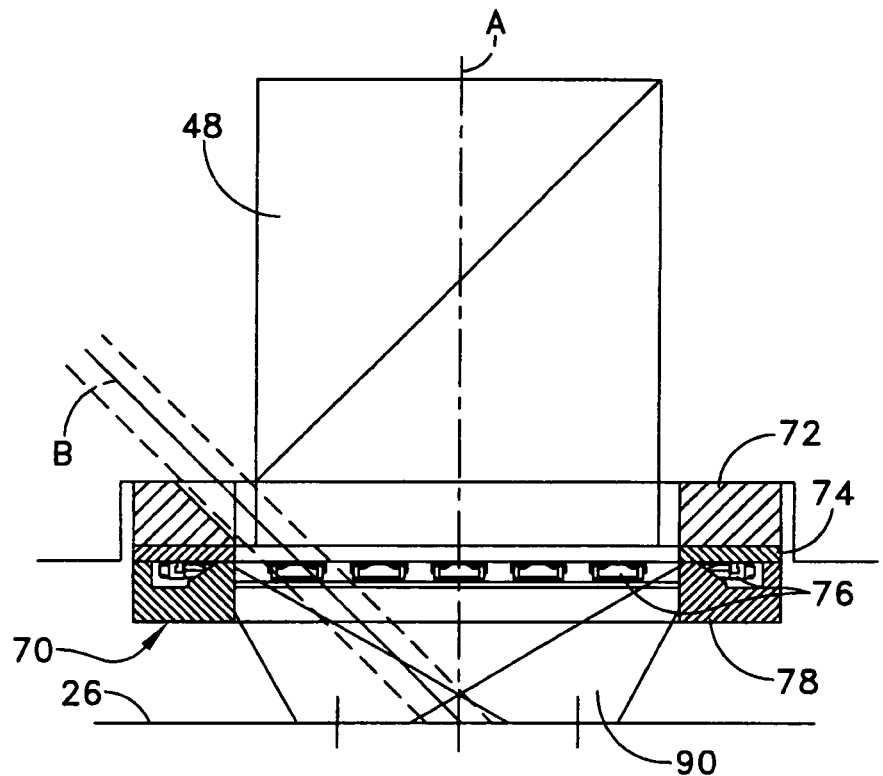
FIG. 6 is a cross-sectional view of the off-axis illumination assembly shown in FIG. 4.

As shown in FIG. 6, and with additional reference to FIGS. 7A, 7B, 8A and 8B, the off-axis illumination assembly 70 includes a rectangular-shaped mounting bracket 72 having four side rails 72a, 72b, 72c, 72d adapted to secure the operable components of the off-axis illumination assembly. In one embodiment, the mounting bracket 72 may be fabricated from a suitable lightweight material, such as aluminum.

Other alternate lightweight materials may be provided, such as plastic or suitable metal alloys. The mounting bracket 72 is attached to the frame 54 of the imaging system 32 directly below the beam splitter 48 by suitable fasteners, such as socket head screws (not shown) through attachment holes 71. The mounting bracket 72 not only supports the components of the off-axis illumination assembly 70, but may further function as a heat sink to absorb heat generated by the off-axis illumination assembly. A pcb substrate 74 is secured to the downwardly facing surface of the mounting bracket 72 to provide power to the off-axis illumination assembly 70, the specific construction of which will be discussed in greater detail below.

The mounting bracket 72 may further include slots 75 to permit light, as used for 3-D triangulation, to pass at an angle onto the target area requiring imaging. The mounting bracket 72 may also provide strain relief for feed wires connected to the off-axis illumination assembly via tight-tolerance wire passages 81 having chamfered reliefs at the pcb substrate interface to minimize the potential of a short circuit.

In certain embodiments, the off-axis illumination assembly 70 comprises a light generating module embodying light emitting diodes, each indicated at 76, the construction of which will be described in greater detail with reference to FIG. 13. The light emitting diodes 76 are secured (e.g., soldered) to the bottom-facing surface of the pcb substrate 74 and, as best shown in FIGS. 8A, 8B, 10A, 10B and 11, are evenly spaced along the lengths of the rails of the mounting bracket 72. The pcb substrate 74 is in electrical communication with a power supply (not shown) to provide energy to the light emitting diodes 76. The light emitting diodes 76 are disposed along a generally horizontal plane that is perpendicular to the vertical axis A of the optical path. The light emitting diodes 76 are directed toward each other along the horizontal plane, and are not directed to the circuit board 26. The manner in which light generated by the light emitting diodes 76 is directed to the circuit board 26 will be discussed in greater detail below.

The off-axis illumination assembly 70 further comprises a lens 78 secured to the mounting bracket 72 to cover the light emitting diodes 76. For example, openings, each indicated at 80, are formed at the four corners of the lens 78 to secure the lens to the mounting bracket 72, e.g., by flat head screws (not shown), with the pcb substrate 74 disposed in between the mounting bracket and the lens. As discussed above, the mounting bracket 72 further includes a plurality of feed-wire attachment holes 81 to provide electrical communication to the pcb substrate 74. The lens 78 is transparent or partially transparent, and in certain embodiments, fabricated from acrylic or glass. For example, the lens 78 may be fabricated from translucent acrylic to reduce object glare. Diffractive properties and the ability of the lens 78 to direct light are maintained when using translucent acrylic. When fabricated from acrylic material, the lens may be injection molded, where at least 1° of draft is required.

Figure 11:
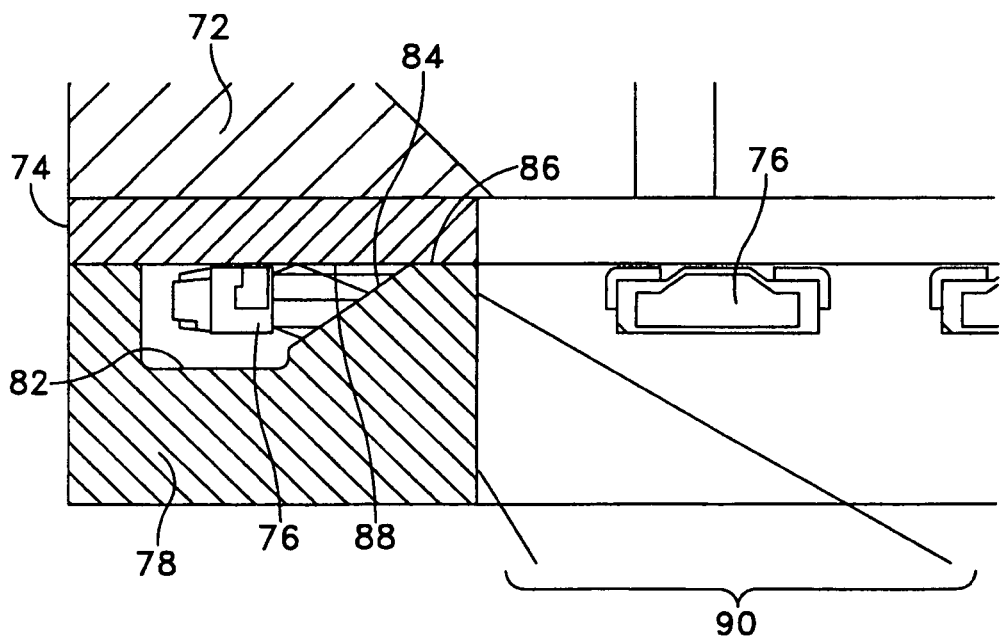
FIG. 11 is an enlarged cross-sectional view of a portion of the off-axis illumination assembly shown in FIG. 6.
Figure 7A:
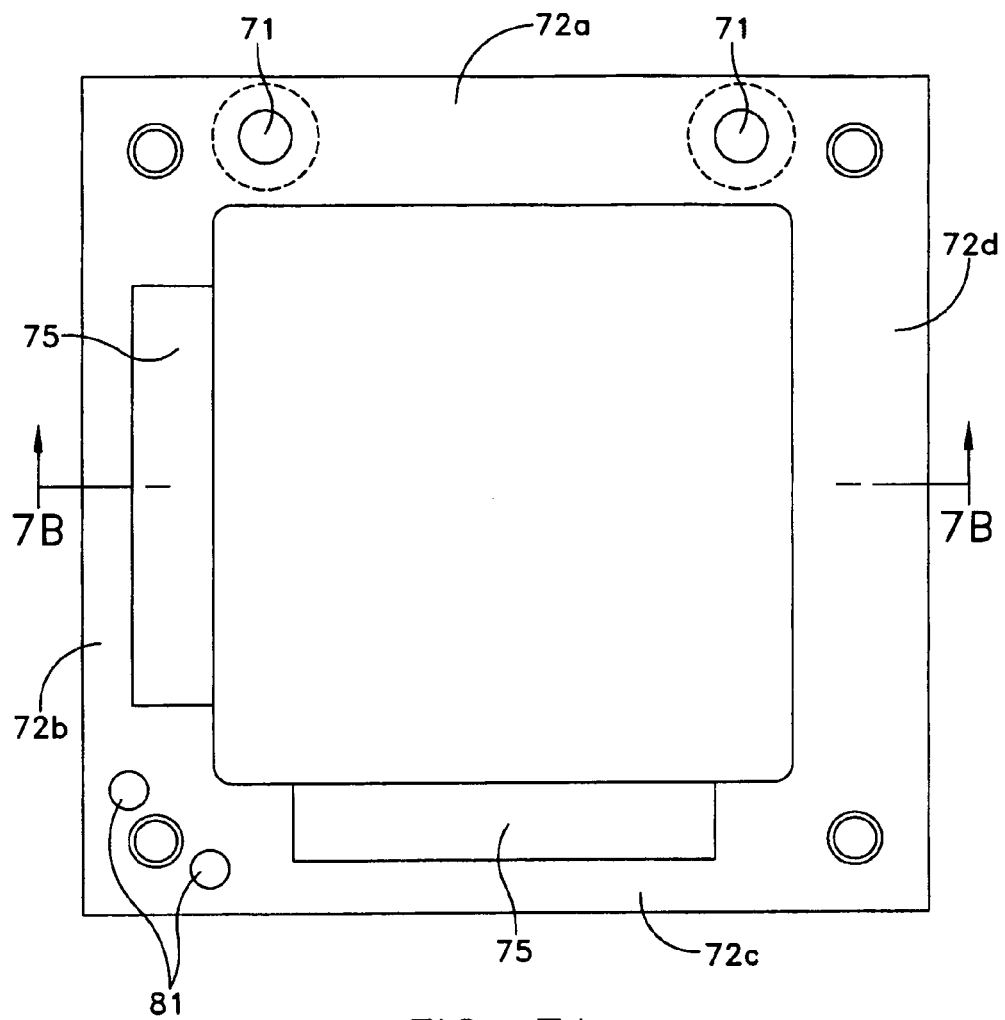
FIG. 7A is a bottom plan view of a mounting bracket of the off-axis illumination assembly.
Figure 7B:
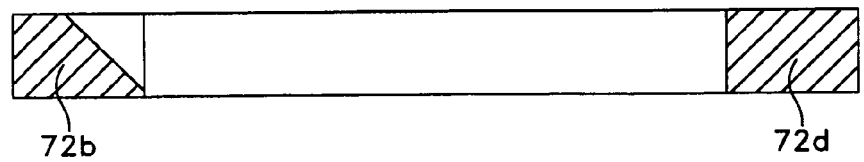
FIG. 7B is a cross-sectional view of the mounting bracket taken along line 7B-7B of FIG. 7A.
Figure 8A:
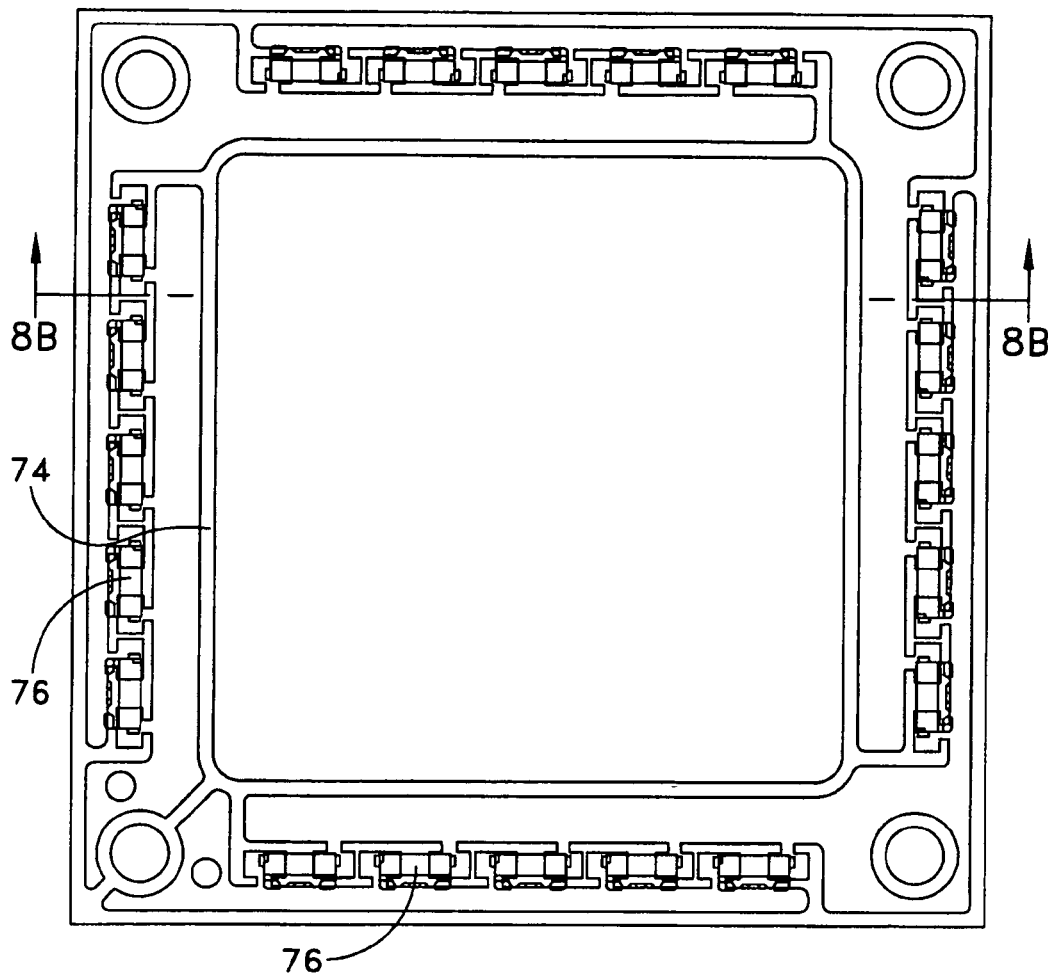
FIG. 8A is a top plan view of a pcb substrate of the off-axis illumination assembly.
Figure 8B:
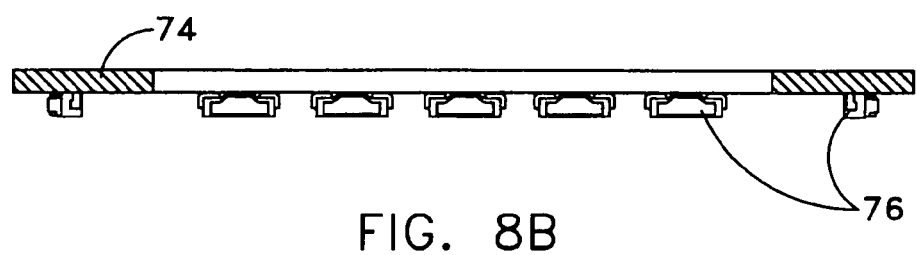
FIG. 8B is a cross-sectional view of the pcb substrate taken along line 8B-8B of FIG. 8A, showing light emitting diodes of the off-axis illumination assembly.
Figure 10A:
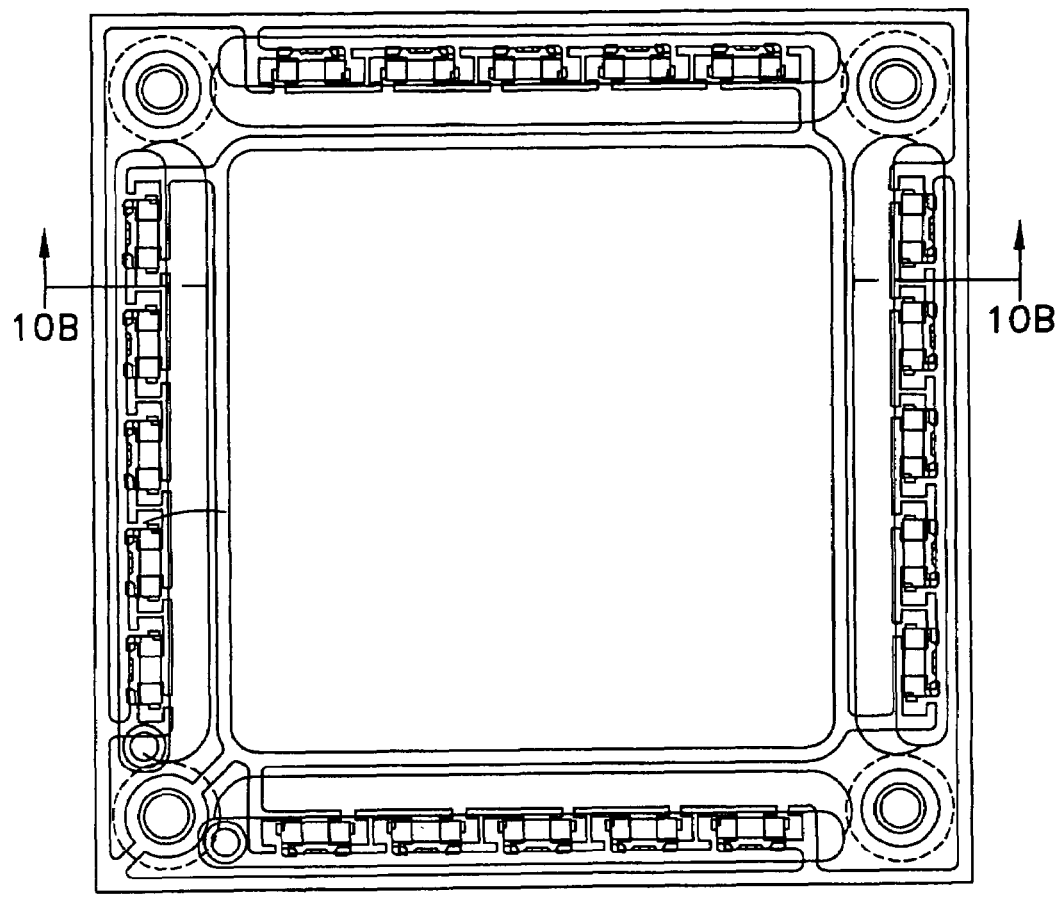
FIG. 10A is a bottom plan view of the off-axis illumination assembly.
Figure 10B:
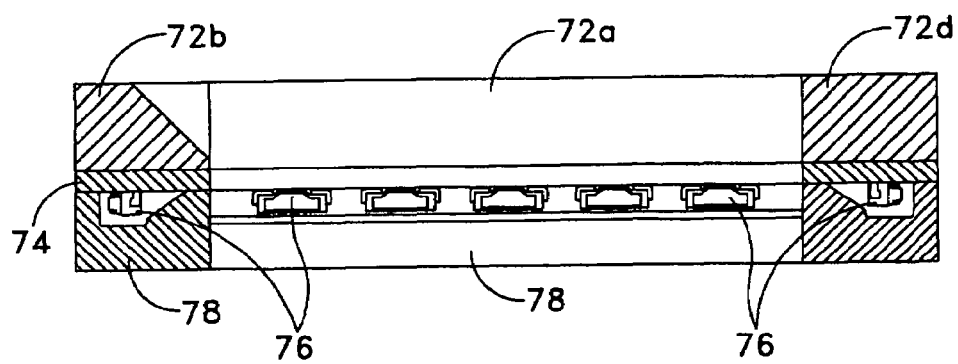
FIG. 10B is a cross-sectional view taken along line 10B-10B of FIG. 10A.

The lens 78 includes four cavities, each indicated at 82 which provide a space for the light emitting diodes 76 along the lengths of each side of the lens. The cavities 82 are also illustrated in FIGS. 10A, 10B and 11. FIG. 10A shows the positioning of the light emitting diodes on the rails of mounting bracket 72. The arrangement is such that the mounting bracket 72, pcb substrate 74, light emitting diodes 76 and lens 78 together define a low profile assembly that fits within the relatively small space provided between the beam splitter 48 and the circuit board 26. In certain embodiments, the total assembly has a thickness of approximately 7 mm, and the nominal clearance between the off-axis illumination assembly 70 and the circuit board 26 is approximately 5 mm. In addition to directing light at a specified angle to a predefined area of the circuit board 26, the lens 78 is also designed to enclose and protect the light emitting diodes 76 and the pcb substrate 74.

Figure 9A:
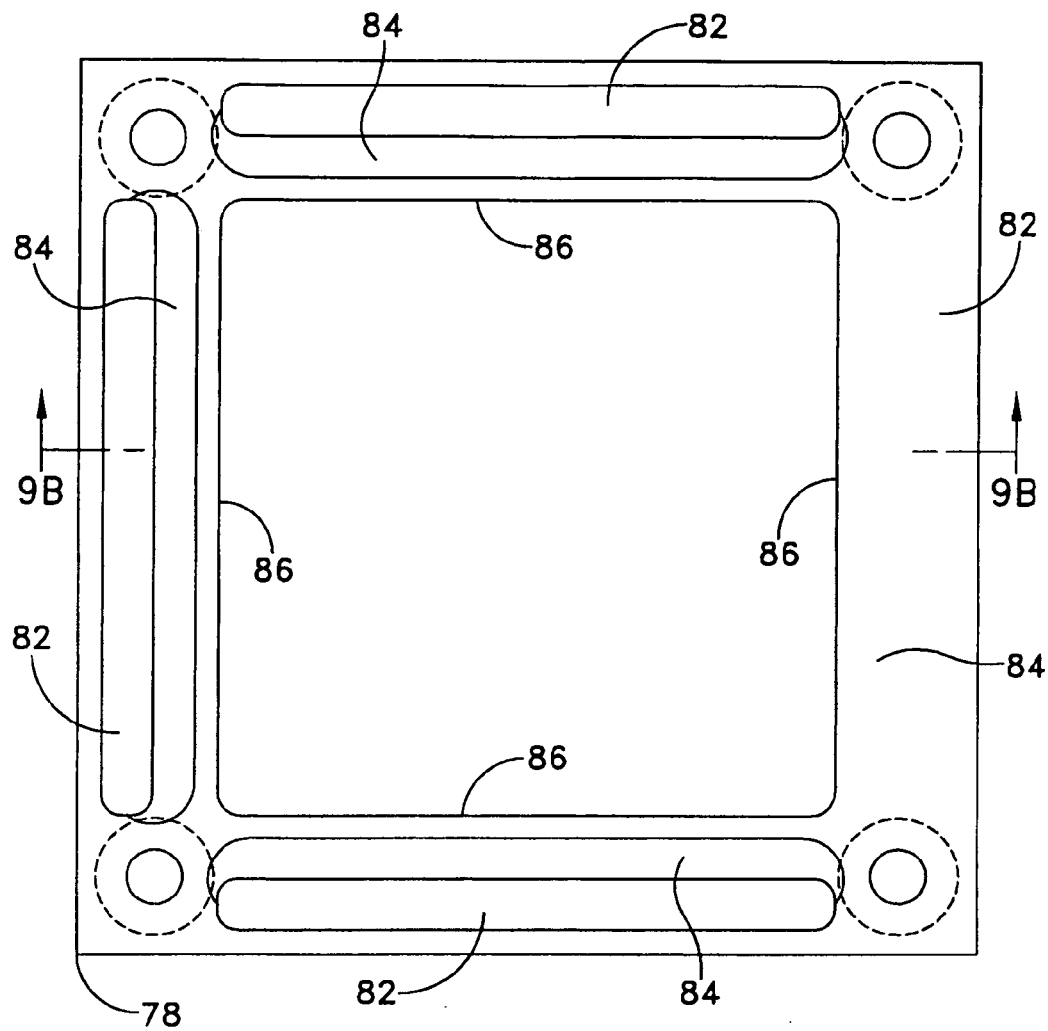
FIG. 9A is a top plan view of a lens of an embodiment of the present invention
Figure 9B:
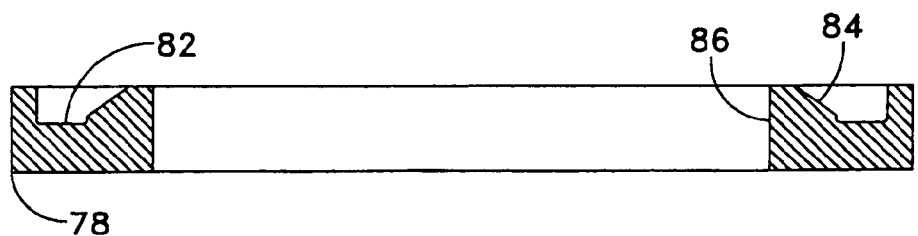
FIG. 9B is a cross-sectional view of the lens taken along line 9B-9B of FIG. 9A.

With specific reference to FIGS. 9A and 9B, each cavity 82 of the lens 78 has a refractive surface 84, which is adapted to direct light from the light emitting diodes 76 through refractive surfaces 84 and 86 and on toward the circuit board 26. Specifically, light directed to the refractive surfaces 84 and 86 is refracted toward the predetermined area of the substrate (circuit board 26) generally along or parallel to axis B thereby providing off-axis illumination with respect to the viewing axis A. As shown, each cavity 82 is sized to receive the light emitting diode comfortably within the cavity. The refractive surface 84 slopes toward a surface 86 of the lens 78 that mates with the underside of the pcb substrate 74. In one embodiment, the index of refraction of the refractive surface 84 is about 1.49. Light directed by the refractive surfaces 84 and 86 may be made to follow a parallel path to provide a constant illumination angle, or may be made to follow a fan-shaped path for a field position dependent angle. As shown, the lens 78 has a thickness of approximately 3 mm.

As shown in FIG. 11, in one embodiment, the light generated by the off-axis illumination assembly 70 follows a generally narrow fan-shaped geometry. The angle of the refractive surfaces 84 and 86 may be modified to change the angle of light propagation and the lens surfaces may be further manipulated to include multiple angles, facets and/or curvatures. For example, the light emitting diodes 76 and the refractive surfaces 84 may be arranged in concentric or curved Fresnel-like sections, or may be arranged in linear, prism-like sections. Portions of light generated by each light emitting diode 76 that travels in a generally upward direction is reflected off of a reflective surface 88 provided on the underside of the pcb substrate 74 in front of the light emitting diode. The reflective surface 88 may be the bare material of the pcb substrate 74, for example. In other embodiments, the reflective surface 88 may be fabricated from a mask material or from ink. In certain other embodiments, the reflective material may be bare copper or gold flashed copper, or a trace or pad having gold flashed copper. With gold flashed copper, oxidation is prevented for consistent reflective performance. In other embodiments, the reflective surface 88 may be a separately applied foil, vinyl, paper or a combination of these materials. The reflective surface 88 may be attached by using glue or a pressure sensitive material, for example. Alternatively, stray light generated by the light emitting diodes 76 may be absorbed by blackened surfaces, if required.

With the shown embodiment, the refractive surface 84 of the lens 78 is approximately at a 55° angle with respect to the vertical axis A. Each light emitting diode 76 produces a geometry of light that is roughly the shape of an elliptical cone. Thus, light directed to the refractive surface 84 and the reflective surface 88 is adapted to be directed to the target or predetermined area of the printed circuit board 26. Any stray light generated by the light emitting diodes 76 may be redirected by reflection or absorbed by blackened surfaces, as required.

It should be understood that a person skilled in the art, given the benefit of this disclosure, may arrange the light emitting diodes 76 in any number of ways. For example, although a rectangular-shaped configuration is illustrated throughout the drawings, other shaped configurations are certainly contemplated. In one example, a circular mounting bracket containing light emitting diodes positioned around a ring may be provided and fall within the scope of the present invention. In another example, the mounting bracket may be elliptical in shape. However, the rectangular shape (e.g., square) of the off-axis illumination assembly 70 offers the minimum physical size while still providing optimum off-axis angles of light to the predetermined area requiring imaging. It should also be understood that a second off-axis illumination assembly may be configured to illuminate the stencil 18 depending on whether the imaging system employs two cameras (see FIG. 4) or one camera (see FIG. 5).

Figure 12:
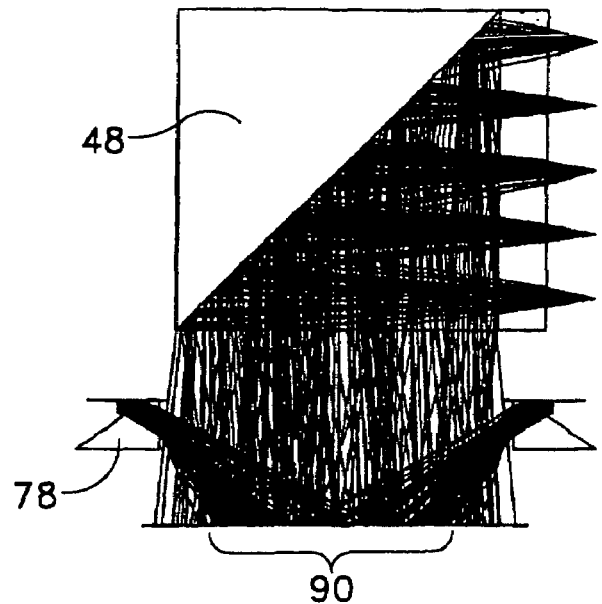
FIG. 12 is a representation of light generated by an on-axis illumination assembly and the off-axis illumination assembly on a substrate.

Referring to FIG. 11, the fan of light 90 generated by a light emitting diode 76 is shown directed to the circuit board 26. A fan of light 90 is generated by each light emitting diode 76 provided around the mounting bracket 72 to splash off-axis light on the circuit board 26. Light directed from the refractive surfaces 84 and 86, and from the reflective surface 88 provide the fan of light 90 that extends generally along or substantially parallel to the axis B, which is disposed at an angle with respect to the viewing axis A and light generated by the on-axis illumination assembly 70. The fan of light 90 generated by the off-axis illumination assembly 70 better illuminates irregular surfaces of solder paste or other substances deposited on the circuit board 26. The fans of light 90 generated by the off-axis illumination assembly and the on-axis light generated by the on-axis illumination assembly are illustrated in FIG. 12.

FIGS. 13A-13D illustrate front, top, bottom and side views, respectively, of a single light emitting diode 76 used in the off-axis illumination assembly 70. As shown, each light emitting diode 76 includes an output face 92 and electrical contacts 94. The output face 92 is the surface through which light is emitted. The electrical contacts 94 are secured to (as by soldering, for example) and in electrical communication with circuit traces (not shown) formed in the pcb substrate 74. In one embodiment, the light emitting diodes 76 are of the type sold by Nichia Corporation of Detroit, Mich. under Model No. NASW008B, with brightness of ranks U2 and V1 having an average brightness of 1500 mcd.

Figure 14:
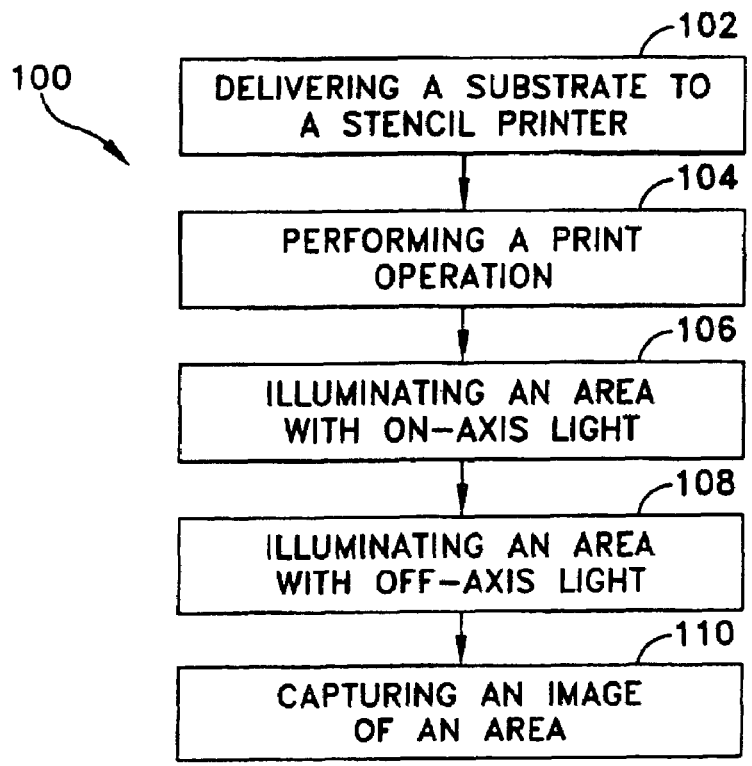
FIG. 14 is a flow diagram of a method of dispensing solder paste onto electronic pads of an electronic substrate of an embodiment of the invention.
Figure 13A:
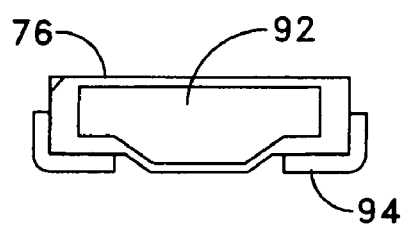
FIGS. 13A-13D are front, top, bottom and side views, respectively, of a light emitting diode of the off-axis illumination assembly.
Figure 13B:
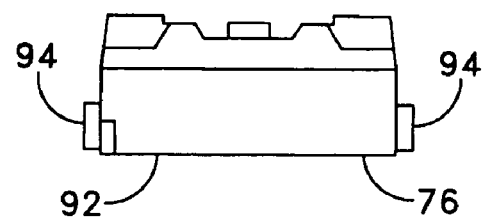
Figure 13C:
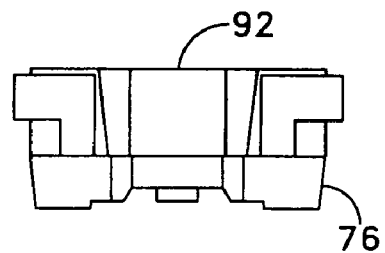
Figure 13D:
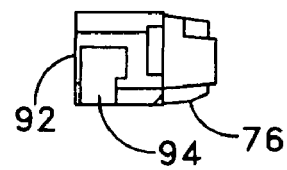

Turning now to FIG. 14, a method for dispensing solder paste onto electronic pads of a circuit board is generally designated at 100. As shown, at 102, a printed circuit board is delivered to a stencil printer via a conveyor system, for example. With reference to FIG. 1, a circuit board is delivered to the print nest via conveyor rails. Once delivered, the circuit board is positioned within a print nest on top of the support assembly, is then precisely aligned with the stencil using the imaging system, and raised by the support assembly so that it is maintained in a print position. Next, the dispensing head is lowered to engage the stencil to deposit solder paste on the circuit board at 104. Once printing is completed, inspection of the circuit board and/or stencil may take place. Stencil inspection may also be performed independently and concurrently as circuit boards are transported to and from the print nest area.

Specifically, a predefined area of the circuit board (or stencil) is imaged by illuminating the predefined area with on-axis light at 106. At the same time, the predefined area may be illuminated with off-axis light at 108. Once the circuit board (or stencil) is adequately illuminated, the camera captures an image of the area at 110.

Next, a subsequent predefined area of the circuit board or the stencil is imaged. The imaging of multiple predefined areas of the circuit board is executed by moving from the first predefined area to the second predefined area. Under the direction of the controller, the imaging system sequentially moves to other predefined areas to capture images for inspection purposes, for example. In other embodiments, the method may include capturing an image of an area of the stencil instead of or in addition to capturing an image of the circuit board.

In one embodiment, the imaging system 32 may be used to perform a texture recognition method, such as the method disclosed in U.S. Pat. No. 6,738,505 to Prince, entitled METHOD AND APPARATUS FOR DETECTING SOLDER PASTE DEPOSITS ON SUBSTRATES, which is owned by the assignee of the present invention and incorporated herein by reference. U.S. Pat. No. 6,891,967 to Prince, entitled SYSTEMS AND METHODS FOR DETECTING DEFECTS IN PRINTED SOLDER PASTE, which is also owned by the assignee of the present invention and incorporated herein by reference, furthers the teachings of U.S. Pat. No. 6,738,505. Specifically, these patents teach texture recognition methods for determining whether solder paste is properly deposited onto predetermined regions, e.g., copper contact pads, located on a printed circuit board.

Figure 15:
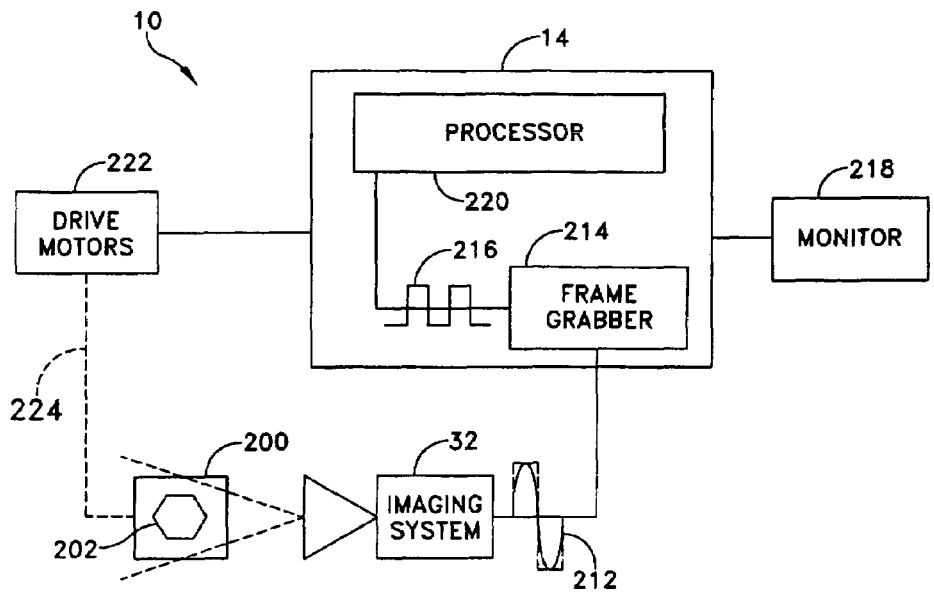
FIG. 15 is a schematic view of an imaging system used to perform a texture recognition method of an embodiment of the invention.
Figures 16, 17:
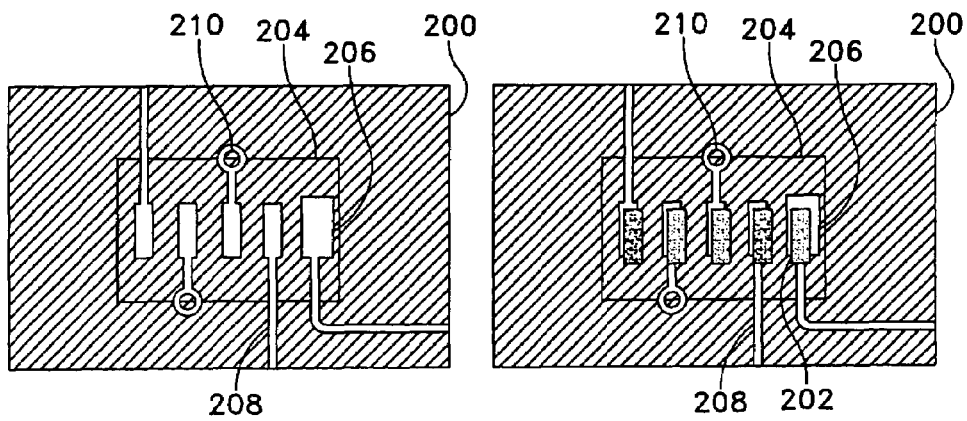
FIG. 16 is a schematic representation of a substrate.
FIG. 17 is a schematic representation of a substrate having solder paste deposited on the substrate.

With reference to FIG. 15, in one embodiment, the screen printer 10 is shown inspecting a substrate 200 having a substance 202 deposited thereon. The substrate 200 may embody a printed circuit board (e.g., circuit board 26), wafer, or similar flat surface, and the substance 202 may embody solder paste, or other viscous materials, such as glues, encapsulents, underfills, and other assembly materials suitable for attaching electronic components onto printed circuit boards or wafers. As shown in FIGS. 16 and 17, the substrate 200 has a region of interest 204 and contact regions 206. The substrate 200 further includes traces 208 and vias 210, which are used to interconnect components mounted on the substrate, for example. FIG. 16 illustrates the substrate 200 without substances deposited on any of the contact regions 206. FIG. 17 illustrates the substrate 200 having substances 202, e.g., solder paste deposits, distributed on the contact regions 206. In the substrate 200, the contact regions 206 are distributed across a designated region of interest 204.

FIG. 17 shows a misalignment of the solder paste deposits 202 with the contact regions 206. As shown, each of the solder paste deposits 202 is partially touching one of the contact regions 206. To ensure good electrical contact and to prevent bridging between adjacent contact regions, e.g., copper contact pads, the solder paste deposits should be aligned to respective contact regions within specific tolerances. Texture recognition methods of the types disclosed in U.S. Pat. Nos. 6,738,505 and 6,891,967 detect misaligned solder paste deposits on contact regions, and as a result, generally improve the manufacturing yield of the substrates.

Referring back to FIG. 15, in one embodiment, a method for solder paste texture recognition includes using the imaging system 32 to capture an image of the substrate 200 having a substance 202 deposited on the substrate. The imaging system 32 may be configured to transmit a real-time signal 212 to an appropriate digital communication port or dedicated frame grabber 214. The digital port may include types commonly known as USB, Ethernet, or Firewire (IEEE 1394). The real-time signal 212 corresponds to an image of the substrate 200 having the substance deposited thereon. Once received, the port or frame grabber 214 creates image data 216 which may be displayed on a monitor 218. In one embodiment, the image data 216 is divided into a predetermined number of pixels, each having a brightness value from 0 to 255 gray levels. In one embodiment, the signal 212 represents a real-time image signal of the substrate 200 and the substance 202 deposited thereon. However, in other embodiments, the image is stored in local memory and transmitted to the controller 14 on demand, as required.

The port or frame grabber 214 is electrically connected to the controller, which includes a processor 220. The processor 220 calculates statistical variations in texture in the image 216 of the substance 202. The texture variations in the image 216 of the substance 202 are calculated independent of relative brightness of non-substance background features on the substrate 200, thereby enabling the processor 220 to determine the location of the substance on the substrate and compare the location of the substance with a desired location. In one embodiment, if the comparison between the desired location and the actual location of the substance 202 reveals misalignment exceeding a predefined threshold, the processor 220 responds with adaptive measures to reduce or eliminate the error, and may reject the substrate or trigger an alarm via the controller. The controller 14 is electrically connected to drive motors 222 of the stencil printer 10 to facilitate the alignment of the stencil 18 and the substrate as well as other motion related to the printing process.

The controller 14 is part of a control loop 224 that includes the drive motors 222 of the stencil printer 10, the imaging system 32, the frame grabber 214 and the processor 220. The controller 14 sends a signal to adjust the alignment of the stencil 18 should the substance 202 be misaligned with the contact region 206.

Thus, it should be observed that the imaging system 32 of the present invention is particularly suited for capturing uniformly illuminated images under a variety of conditions as required to perform texture recognition methods while providing efficient real-time, closed-loop control. Also, since the additional light afforded by the off-axis illumination system enables shorter exposure times, the imaging system is able to more quickly image regions of interest (predefined areas) so that data can be more quickly analyzed.

During operation, when depositing a substance on a substrate, an image is captured of the substance deposit. In one embodiment, the substance is solder paste and the substrate is a printed circuit board. The image of the substrate with the substance may be captured in real-time or retrieved from memory of the controller 14. The image is sent to the processor 220 of the controller 14 in which texture variations in the image are detected. These texture variations are used to determine the location of the substance on the substrate. The processor 220 is programmed to compare the particular location of the substance with predetermined locations of the substrate. If variations are within predetermined limits, the processor 220 may respond with adaptive measures to refine the process. If the variations lie outside predetermined limits, then an appropriate recovery measure may be employed in which the substrate is rejected, the process is terminated, or an alarm is triggered. The controller 14 is programmed to perform any one or more of these functions if a defect is detected.

In one embodiment, the stencil 18 and/or the circuit board 26 may move relative to the imaging system 32 to take images of the stencil and the board, respectively. For example, the stencil 18 may be translated away from the print nest and moved over or under the imaging system 32, which may be stationary. Similarly, the circuit board 26 may be shuttled away from the print nest and moved over or under the imaging system 32. The camera (e.g., camera 36) of the imaging system 32 may then take an image of the stencil 18 and/or circuit board 26 in the manner described above.

In another embodiment, the imaging system 32 may be employed within a dispenser designed to dispense viscous or semi-viscous materials, such as solder paste, glues, encapsulents, underfills, and other assembly materials on a substrate, such as a printed circuit board. Such dispensers are of the type sold by Speedline Technologies, Inc., under the brand name CAMALOT®.

It should be observed that by adding greater off-axis illumination increases the reflectivity and thus the relative brightness of irregular or non-orthogonal surfaces of poorly shaped solder paste deposits. By adding off-axis illumination, the strongest components of scattered light from these surfaces is more likely to be directed toward the optical viewing path where the light may be collected and used by the imaging system 32 to create an image. The added efficiency of illumination afforded by the off-axis illumination assembly reduces the time required to acquire images.

The off-axis illumination assembly 70 of embodiments of the off-axis illumination invention is designed to supplement deficiencies with on-axis illumination in that the off-axis illumination tends to highlight irregular, angled, faceted or otherwise less than ideal solder paste surfaces that would not be as effectively illuminated or sufficiently filled-in by using on-axis illumination alone. The assembly 70 of embodiments of the invention has a low profile so that it is small enough to fit within the limited space available between existing vision probe hardware and the circuit board or other surface requiring illumination. It should be noted that sufficient additional clearance must be provided to ensure consistent collision-free movement of the inspection system above a circuit board having non-planar geometry or components mounted thereon. The off-axis illumination assembly is capable of directing light onto the circuit board or other surface at extremely close working distances while maintaining considerable control of local angles of incidence and the distribution and balance of light across the target area.

As a result, the provision of the off-axis illumination assembly 70 of embodiments of the invention improves the robustness of two-dimensional solder paste inspection, especially in circumstances where there is less than ideal solder paste deposit geometry. In some applications, this condition may be persistent and somewhat stabilized without producing significant defects that would adversely affect subsequent processes. However, poorly defined solder paste deposits usually indicate the presence of significant defects and trends that, if left unchecked, might eventually lead to catastrophic circuit board defects. The off-axis illumination assembly is particularly designed to improve the ability to view such defects.

In other embodiments, it should be observed that the off-axis illumination assembly 70 may be used to direct off-axis illumination toward the stencil 18. Specifically, an off-axis illumination assembly, identical to assembly 70, may be configured or assembled on beam splitter 50, in the same manner that assembly 70 is mounted on beam splitter 48.

While this invention has been shown and described with references to particular embodiments thereof, those skilled in the art will understand that various changes in form and details may be made therein without departing from the scope of the invention, which is limited only to the following claims.

What is claimed is:

1. A stencil printer for depositing solder paste onto a surface of an electronic substrate, the stencil printer comprising:
   a frame;
   a substrate support coupled to the frame, the substrate support being constructed and arranged to support an electronic substrate;
   a stencil coupled to the frame, the stencil having a plurality of apertures formed therein;

a dispenser coupled to the frame, the stencil and the dispenser being constructed and arranged to deposit solder paste onto the electronic substrate;

an imaging system constructed and arranged to capture an image of the electronic substrate, the imaging system comprising a camera assembly, an on-axis illumination assembly adapted to generate light substantially along a first axis generally perpendicular to the surface of the electronic substrate, an off-axis illumination assembly adapted to generate rays of light substantially along a second axis extending at an angle with respect to the first axis, the off-axis illumination assembly including a light generating module and a lens configured to direct the rays of light, and a mounting bracket adapted to support the light generating module and the lens of the off-axis illumination assembly; and a controller coupled to the imaging system, the controller being constructed and arranged to control movement of the imaging system to capture an image, wherein the imaging system is configured to operate between the stencil and the substrate support.

2. The stencil printer of claim 1, wherein the on-axis illumination assembly of the imaging system further comprises an optical path adapted to direct light between the on-axis illumination assembly, the electronic substrate, and the camera assembly.

3. The stencil printer of claim 2, wherein the camera assembly comprises a camera and a lens assembly adapted to direct an image to the camera.

4. The stencil printer of claim 2, wherein the optical path comprises a beam splitter and a minor.

5. The stencil printer of claim 1, wherein the light generating module comprises at least one light emitting diode.

6. The stencil printer of claim 1, wherein the lens comprises one or more refractive surfaces adapted to direct light from the light generating module along a prescribed path.

7. The stencil printer of claim 1, wherein the on-axis illumination assembly comprises at least one light emitting diode.

8. The stencil printer of claim 1, wherein the imaging system is constructed and arranged to capture an image of solder paste on a pad of the electronic substrate within the area.

9. The stencil printer of claim 1, wherein the controller comprises a processor programmed to perform texture recognition of the electronic substrate to determine the accuracy of the solder paste deposits on the pads of the electronic substrate.

10. An imaging system for capturing an image of a surface of an electronic substrate, the imaging system comprising:

a housing including mounting bracket;

a camera assembly coupled to the housing, the camera assembly being adapted to capture an image of the electronic substrate;

an on-axis illumination assembly coupled to the housing, the on-axis illumination assembly being adapted to generate light substantially along a first axis generally perpendicular to the surface of the electronic substrate; and an off-axis illumination assembly coupled to the bracket of the housing, the off-axis illumination assembly being adapted to generate rays of light substantially along a second axis extending at an angle with respect to the first axis, the off axis illumination assembly including a light generating module and a lens configured to direct the rays of light, the light generating module and the lens being supported by the mounting bracket, wherein the imaging system is configured to operate between a stencil and a substrate support of a stencil printer.

11. The imaging system of claim 10, further comprising an optical path adapted to direct light between the on-axis illumination assembly, the electronic substrate, and the camera assembly.

12. The imaging system of claim 11, wherein the optical path comprises at least one beam splitter and a mirror.

13. The imaging system of claim 11, wherein the camera assembly comprises a camera and a lens assembly adapted to direct an image to the camera.

14. The imaging system of claim 11, wherein the on-axis illumination assembly comprises at least one light emitting diode.

15. The imaging system of claim 11, wherein the imaging system is constructed and arranged to capture an image of solder paste on a pad of an electronic substrate.

16. The imaging system of claim 10, wherein the light generating module comprises at least one light emitting diode.

17. The imaging system of claim 10, wherein the lens comprises a refractive surface adapted to direct light from the light generating module to create the rays of light.

18. A method for dispensing solder paste onto a surface of an electronic substrate, the method comprising:

delivering an electronic substrate to a stencil printer;

supporting the electronic substrate;

performing a print operation with a stencil to print solder paste onto the surface of the electronic substrate;

positioning an imaging system between stencil and the electronic substrate;

illuminating at least one area of the electronic substrate with on-axis light that extends substantially along a first axis generally perpendicular to the surface of the electronic substrate;

illuminating the at least one area of the electronic substrate with a lens configured to direct off-axis light substantially along a second axis extending at an angle with respect to the first axis; and capturing an image of the at least one area of the electronic substrate with the imaging system.

19. The method of claim 18, further comprising:

positioning the electronic substrate in a print position; and positioning a stencil onto the electronic substrate.

20. The method of claim 18, further comprising moving the imaging system from a first position that captures an image of a first area to a second position that captures an image of a second area.

21. The method of claim 18, further comprising performing a texture recognition sequence of the at least one area of the electronic substrate to determine the accuracy of the solder paste deposits on the pads of the electronic substrate.

22. The method of claim 18, further comprising illuminating the at least one area of the electronic substrate with off-axis light that extends substantially along a third axis extending at an angle with respect to the first axis.

23. A stencil printer for depositing solder paste onto a surface of an electronic substrate, the stencil printer comprising:

a frame;

a stencil coupled to the frame, the stencil having a plurality of apertures formed therein;

a substrate support coupled to the frame, the substrate support being constructed and arranged to support an electronic substrate;

a dispenser coupled to the frame, the stencil and the dispenser being constructed and arranged to deposit solder paste onto the electronic substrate;

an imaging system constructed and arranged to capture an image of the electronic substrate, the imaging system comprising a camera assembly, an on-axis illumination assembly adapted to generate light substantially along a first axis generally perpendicular to the surface of the electronic substrate, the on-axis illumination assembly including an optical path adapted to reflect light between the on-axis illumination assembly, the electronic substrate, and the camera assembly, means for generating rays of light along a second axis extending substantially at an angle with respect to the first axis, the means for generating rays of light including a light generating module and a lens configured to direct the rays of light, and a mounting bracket adapted to support the light generating module and the lens of the means foe generating rays of light; and a controller coupled to the imaging system, the controller being constructed and arranged to control movement of the imaging system to capture an image, wherein the imaging system is configured to operate between the stencil and the substrate support.

24. The stencil printer of claim 23, wherein the means for generating rays of light comprises an off-axis illumination assembly.

25. The stencil printer of claim 23, wherein the light generating module comprises a light emitting diode.

26. The stencil printer of claim 23, wherein the lens comprises at least one surface adapted to direct light from the light generating module to create the rays of light.

27. The stencil printer of claim 23, wherein the camera assembly comprises a camera and a lens assembly adapted to direct an image to the camera.

* * * * *